United States Patent
Matsuda et al.

(10) Patent No.: US 6,897,330 B2
(45) Date of Patent: May 24, 2005

(54) FLUORINATED AMIDE COMPOUNDS AND THEIR PREPARATION

(75) Inventors: Takashi Matsuda, Gunma-ken (JP); Noriyuki Koike, Gunma-ken (JP); Yasunori Sakano, Gunma-ken (JP)

(73) Assignee: Shin-Etsu Chemical Co., LTD, Tokyo (JP)

( * ) Notice: Subject to any disclaimer, the term of this patent is extended or adjusted under 35 U.S.C. 154(b) by 279 days.

(21) Appl. No.: 10/216,896

(22) Filed: Aug. 13, 2002

(65) Prior Publication Data

US 2003/0069436 A1 Apr. 10, 2003

(30) Foreign Application Priority Data

Aug. 14, 2001 (JP) ........................................ 2001-245891

(51) Int. Cl.$^7$ ................................................. C07E 7/10
(52) U.S. Cl. ........................................................ 556/419
(58) Field of Search ......................................... 556/419

(56) References Cited

U.S. PATENT DOCUMENTS 5,665,846 A * 9/1997 Sato et al. ..................... 528/15
5,705,591 A * 1/1998 Matsuda et al. ............... 528/42

* cited by examiner

Primary Examiner—Peter O'Sullivan
(74) Attorney, Agent, or Firm—Birch, Stewart, Kolasch & Birch, LLP

(57) ABSTRACT

Novel fluorinated amide compounds having siloxane bonds or silalkylene bonds, when crosslinked with organic peroxides, yield fluoro-rubber having excellent chemical resistance and solvent resistance.

2 Claims, 2 Drawing Sheets

FLUORINATED AMIDE COMPOUNDS AND THEIR PREPARATION

This invention relates to fluorinated amide compounds used in the manufacture of fluorinated rubber and a process for preparing the same.

BACKGROUND OF THE INVENTION

Prior art known fluorinated amide compounds include those of the following formula (i).

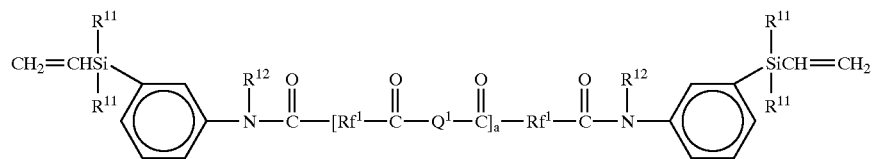

(i)

Herein $R^{11}$ is a substituted or unsubstituted monovalent hydrocarbon group, $R^{12}$ is hydrogen or a substituted or unsubstituted monovalent hydrocarbon group, $Q^1$ is a group of the following general formula (ii) or (iii):

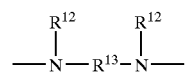

(ii)

wherein $R^{13}$ is a substituted or unsubstituted divalent hydrocarbon group which may be separated by an oxygen, nitrogen and/or silicon atom, and $R^{12}$ is as defined above,

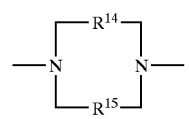

(iii)

wherein $R^{14}$ and $R^{15}$ each are a substituted or unsubstituted divalent hydrocarbon group, $Rf^1$ is a divalent perfluoroalkylene or divalent perfluoropolyether group, and "a" is an integer inclusive of 0.

It would be desirable to have siloxane or silalkylene bond-bearing fluorinated amide compounds which yield fluorinated rubber having excellent chemical resistance and solvent resistance.

SUMMARY OF THE INVENTION

It has been found that a novel fluorinated amide compound of the general formula (1) is obtained by effecting hydrosilylation reaction of a compound of the general formula (9) with a compound of the general formula (10), the formulae being defined later; that a fluorinated rubber having excellent chemical resistance and solvent resistance is obtained by subjecting the fluorinated amide compound to radical crosslinking with the aid of an organic peroxide, for example; that when the fluorinated amide compound has an unsaturated bond within its molecule, a fluorinated rubber having excellent chemical resistance and solvent resistance is obtained by reacting the fluorinated amide compound with a SiH group-containing compound in the presence of a platinum group catalyst; and that the fluorinated amide compound is otherwise applicable as a pressure-sensitive adhesive, binder, coating or agent having excellent chemical resistance and solvent resistance.

The present invention provides a fluorinated amide compound of the following general formula (1).

$$A—(Rf—Q)_n—Rf—A \qquad (1)$$

Herein Rf is a divalent perfluoroalkylene group $C_mF_{2m}$ wherein m is an integer of 2 to 15, or a divalent perfluorooxy-alkylene group selected from groups of the following formulae (2), (3) and (4):

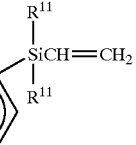

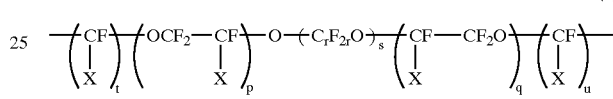

(2)

wherein X is each independently F or $CF_3$, p and q each are an integer of 0 to 200, r is an integer of 2 to 6, s is an integer of 1 to 6, t and u each are 1 or 2,

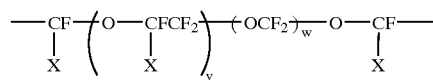

(3)

wherein X is as defined above, v and w each are an integer of 1 to 100,

$$—CF_2CF_2—(OCF_2CF_2CF_2)_y—OCF_2CF_2— \qquad (4)$$

wherein y is an integer of 1 to 200.

A is a monovalent organic group of the following formula (5) or (6):

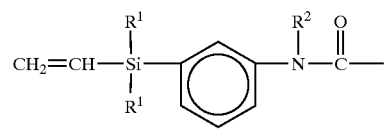

(5)

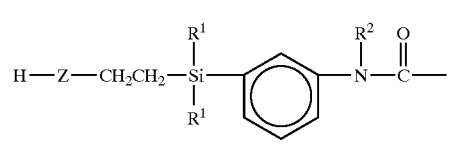

(6)

wherein $R^1$ is a monovalent hydrocarbon group selected from among alkyl, cycloalkyl, aryl, aralkyl groups of 1 to 10 carbon atoms and substituted ones of the foregoing groups in which some or all of the hydrogen atoms are substituted with halogen atoms, $R^2$ is hydrogen or a monovalent hydrocarbon group selected from among alkyl, cycloalkyl, aryl, aralkyl groups of 1 to 10 carbon atoms and substituted ones of the foregoing groups in which some or all of the hydrogen atoms are substituted with halogen atoms, Z is a divalent organic group of the formula (7):

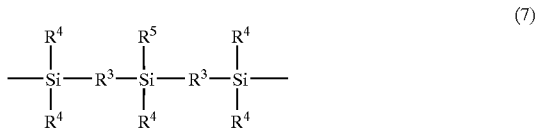
(7)

wherein $R^3$ is an oxygen atom or a divalent hydrocarbon group selected from among alkylene, cycloalkylene, arylene groups of 1 to 8 carbon atoms, substituted ones of the foregoing groups in which some of the hydrogen atoms are substituted with halogen atoms, and combinations of alkylene with arylene, $R^4$ is a monovalent hydrocarbon group selected from among alkyl, cycloalkyl, aryl, aralkyl groups of 1 to 10 carbon atoms and substituted ones of the foregoing groups in which some or all of the hydrogen atoms are substituted with halogen atoms, $R^5$ is a monovalent hydrocarbon group selected from among alkyl, cycloalkyl, aryl, aralkyl groups of 1 to 10 carbon atoms, aliphatic unsaturation-bearing monovalent hydrocarbon groups of 2 to 20 carbon atoms, and substituted ones of the foregoing groups in which some or all of the hydrogen atoms are substituted with halogen atoms.

Q is a divalent organic group of the following formula (8):

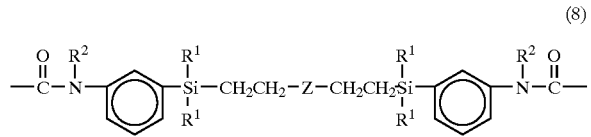
(8)

wherein $R^1$, $R^2$ and Z are as defined above. The subscript n is an integer of at least 1.

The present invention also provides a process of preparing a fluorinated amide compound of the general formula (1), comprising the step of effecting hydrosilylation reaction of a compound of the general formula (9) with a compound of the general formula (10):

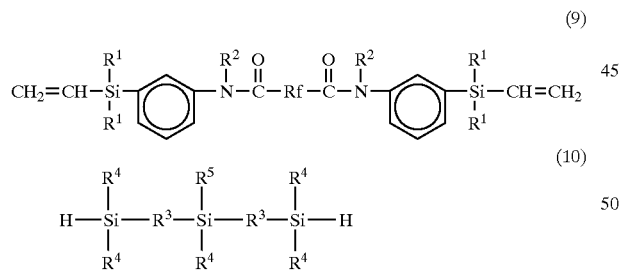
(9)

(10)

wherein $R^1$ to $R^5$ and Rf are as defined above.

DESCRIPTION OF THE PREFERRED EMBODIMENTS

Figure 1:
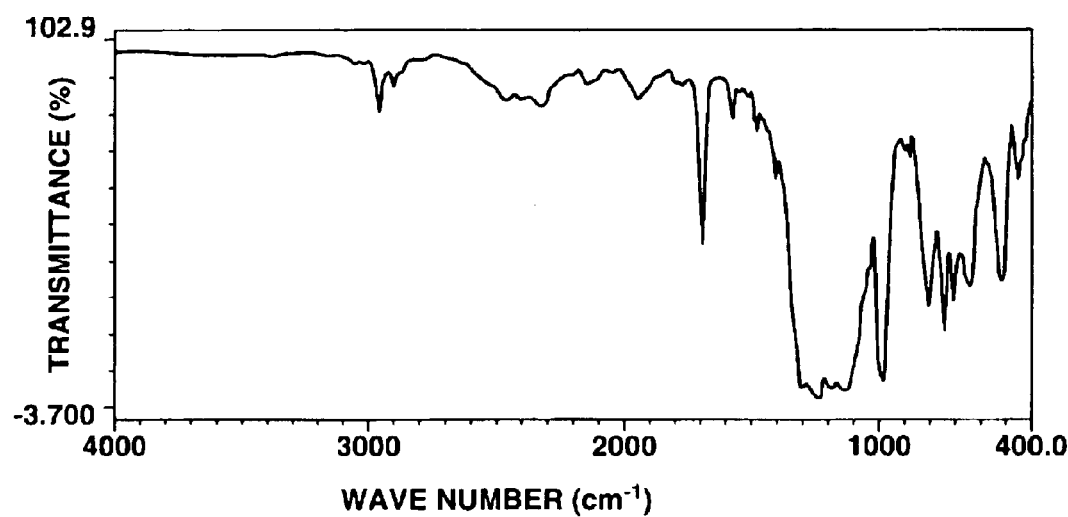
FIGS. 1, 2 and 3 are diagrams showing IR spectra of the compounds prepared in Examples 1, 2 and 3, respectively.

The fluorinated amide compounds of the present invention have the following general formula (1).

(1)

Herein Rf is a divalent perfluoroalkylene group: $C_mF_{2m}$ wherein m is an integer of 2 to 15, or a divalent perfluorooxyalkylene group selected from groups of following formulae (2), (3) and (4).

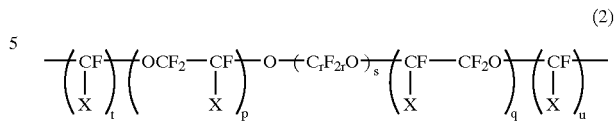
(2)

Herein X is each independently F or $CF_3$; p and q each are an integer of 0 to 200, preferably 1 to 100, and p+q is preferably 2 to 200; r is an integer of 2 to 6, s is an integer of 1 to 6, t and u each are an integer of 1 or 2.

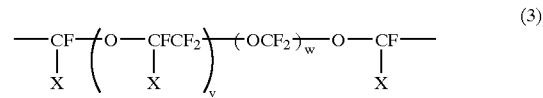
(3)

Herein X is as defined above, v and w each are an integer of 1 to 100, preferably 1 to 50.

(4)

Herein y is an integer of 1 to 200, preferably 1 to 100.

The divalent perfluoroalkylene groups may be straight or branched and include, for example, $-C_2F_4-$, $-C_3F_6-$, $-C_4F_8-$, $-C_6F_{12}-$, $-C_8F_{16}-$, $-C_{10}F_{20}-$ and $-C_2F_4CF(CF_3)C_4F_8-$.

Examples of suitable divalent perfluorooxyalkylene groups are given below.

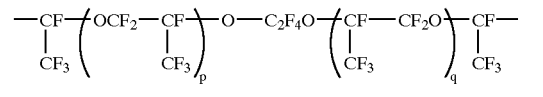

p + q = 2 to 200

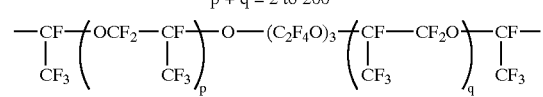

p + q = 2 to 200

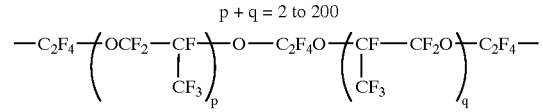

p + q = 2 to 200

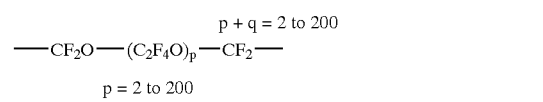

p = 2 to 200

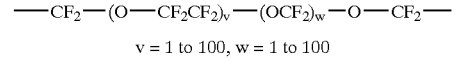

v = 1 to 100, w = 1 to 100

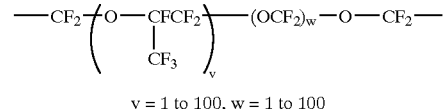

v = 1 to 100, w = 1 to 100

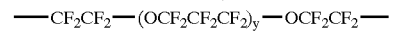

y = 1 to 200

In formula (1), A is a monovalent organic group of the following formula (5) or (6).

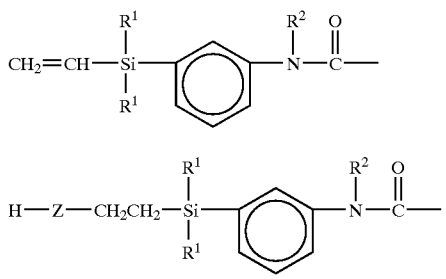

(5)

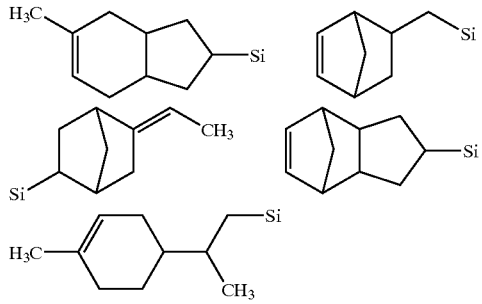

(6)

In formulae (5) and (6), $R^1$ is a monovalent hydrocarbon group selected from among alkyl, cycloalkyl, aryl, aralkyl groups of 1 to 10 carbon atoms and substituted ones of the foregoing groups in which some or all of the hydrogen atoms are substituted with halogen atoms; $R^2$ is hydrogen or a monovalent hydrocarbon group selected from among alkyl, cycloalkyl, aryl, aralkyl groups of 1 to 10 carbon atoms and substituted ones of the foregoing groups in which some or all of the hydrogen atoms are substituted with halogen atoms; and Z is a divalent organic group of the following formula (7).

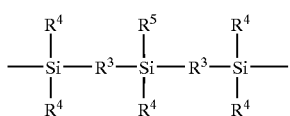

(7)

In formula (7), $R^3$ is an oxygen atom or a divalent hydrocarbon group selected from among alkylene, cycloalkylene, arylene groups of 1 to 8 carbon atoms, substituted ones of the foregoing groups in which some of the hydrogen atoms are substituted with halogen atoms, and combinations of alkylene with arylene; $R^4$ is a monovalent hydrocarbon group selected from among alkyl, cycloalkyl, aryl, aralkyl groups of 1 to 10 carbon atoms and substituted ones of the foregoing groups in which some or all of the hydrogen atoms are substituted with halogen atoms; $R^5$ is a monovalent hydrocarbon group selected from among alkyl, cycloalkyl, aryl, aralkyl groups of 1 to 10 carbon atoms, aliphatic unsaturation-bearing monovalent hydrocarbon groups of 2 to 20 carbon atoms, and substituted ones of the foregoing groups in which some or all of the hydrogen atoms are substituted with halogen atoms.

Suitable monovalent hydrocarbon groups represented by $R^1$, $R^2$ and $R^4$ include alkyl groups such as methyl, ethyl, propyl, isopropyl, butyl, isobutyl, tert-butyl, hexyl, octyl, and decyl; cycloalkyl groups such as cyclopentyl, cyclohexyl and cycloheptyl; aryl groups such as phenyl, tolyl, xylyl and naphthyl; aralkyl groups such as benzyl, phenylethyl, phenylpropyl and methylbenzyl; and substituted ones of the foregoing groups in which some or all of the hydrogen atoms are substituted with halogen atoms, such as chloromethyl, chloropropyl, bromoethyl and trifluoropropyl.

Examples of the alkyl, cycloalkyl, aryl and aralkyl groups of 1 to 10 carbon atoms and halogenated ones thereof represented by $R^5$ are the same as enumerated above.

Examples of the aliphatic unsaturation-bearing monovalent hydrocarbon groups represented by $R^5$ are vinyl, propenyl, isopropenyl, butuenyl, isobutenyl, hexenyl, cyclohexenyl, and groups of the following structures (wherein Si is depicted for indicating the position at which the structure is bonded to silicon), and substituted ones of the foregoing groups in which some or all of the hydrogen atoms are substituted with halogen atoms.

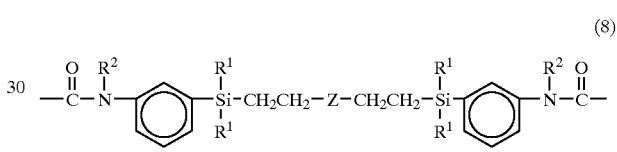

$R^3$ is an oxygen atom or a divalent hydrocarbon group of 1 to 8 carbon atoms. Examples of the divalent hydrocarbon group represented by $R^3$ include alkylene groups such as methylene, ethylene, propylene, methylethylene, butylene, and hexamethylene; cycloalkylene groups such as cyclohexylene; arylene groups such as phenylene, tolylene and xylylene; substituted ones of the foregoing groups in which some of the hydrogen atoms are substituted with halogen atoms; and combinations of alkylene with arylene.

Again in formula (1), Q is a divalent organic group of the following formula (8).

(8)

$$-\overset{O}{\underset{\|}{C}}-\overset{R^2}{\underset{|}{N}}-\underset{}{\bigcirc}-\overset{R^1}{\underset{|}{Si}}-CH_2CH_2-Z-CH_2CH_2-\overset{R^1}{\underset{|}{Si}}-\underset{}{\bigcirc}-\overset{R^2}{\underset{|}{N}}-\overset{O}{\underset{\|}{C}}-$$

Herein $R^1$, $R^2$ and Z are as defined above.

In formula (1), n is an integer of at least 1, preferably 2 to 200, more preferably 5 to 100, and most preferably 8 to 80. Accordingly, the compound of formula (1) preferably has a number average molecular weight (Mn) of about 20,000 to 2,000,000, and more preferably 50,000 to 1,000,000, and a kinematic viscosity of about 2 to 100 mm$^2$/s, especially about 10 to 50 mm$^2$/s in a 10 wt % solution thereof in nonafluorobutyl methyl ether ($C_4F_9OCH_3$).

The fluorinated amide compound of formula (1) according to the invention can be prepared by reacting a compound of the general formula (9) with a compound of the general formula (10) in the presence of a hydrosilylation reaction catalyst.

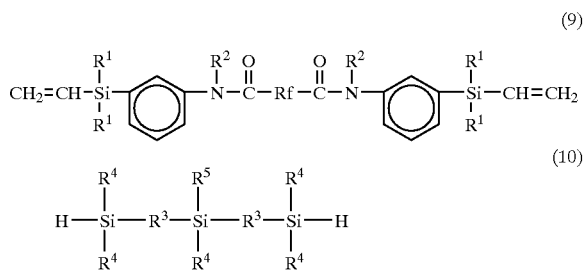

Herein $R^1$ to $R^5$ and Rf are as defined above.

A reaction proportion between the compound of formula (9) and the compound of formula (10) is desirably set to a molar ratio (9)/(10) of from 2/3 to 3/2, and most desirably a molar ratio (9)/(10) close to 1/1.

The hydrosilylation reaction catalysts used herein are preferably transition metals, for example, platinum group metals such as Pt, Rh and Pd and transition metal compounds.

Since these compounds are generally noble metal compounds which are expensive, platinum compounds are often used because of ease of availability.

Exemplary platinum compounds include, but are not limited thereto, chloroplatinic acid, complexes of chloroplatinic acid with olefins such as ethylene, complexes of chloroplatinic acid with alcohols or vinylsiloxanes, and platinum on silica, alumina or carbon.

Suitable platinum group metal compounds other than platinum compounds include rhodium, ruthenium, iridium and palladium compounds such as $RhCl(PPh_3)_3$, $RhCl(CO)(PPh_3)_2$, $RhCl(C_2H_4)_2$, $Ru_3(CO)_{12}$, $IrCl(CO)(PPh_3)_2$, and $Pd(PPh_3)_4$ wherein Ph stands for phenyl.

The amount of the catalyst used is not critical and is preferably determined from the standpoints of economy and effective reaction so as to provide 0.1 to 1,000 ppm, more preferably 0.1 to 500 ppm of platinum group metal based on the weight of the reactants combined.

The reaction temperature may be in the range of 0 to 200° C., and preferably 50 to 150° C. The reaction time varies over a wide range and is usually about 5 minutes to 2 hours.

The reaction may be carried out in a diluted state using an organic solvent as long as the solvent does not adversely affect hydrosilylation. The organic solvent, if used, is preferably a partially or entirely fluorine-modified organic solvent.

As understood from the foregoing description, the fluorinated amide compound obtained by the above process is terminated with an end group of formula (11) or (12).

$$CH_2=CH— \quad (11)$$

$$H—Z—CH_2CH_2— \quad (12)$$

Most often, these end groups of formulae (11) and (12) are admixed at the terminus of the resulting compound. Particularly when the compounds of formulae (9) and (10) are reacted in equimolar amounts, the end groups of formulae (11) and (12) are admixed in an equimolar state at the terminus of the resulting compound, but in trace amounts which are undetectable by ordinary analysis means such as IR and NMR.

By combining the fluorinated amide compound of the invention with a crosslinking agent such as an organic peroxide for inducing radical crosslinking, a rubber having good chemical resistance and solvent resistance is obtained. When the fluorinated amide compound has an unsaturated bond within its molecule, a fluorinated rubber having excellent chemical resistance and solvent resistance is obtained by reacting the fluorinated amide compound with a SiH group-containing compound in the presence of a platinum group catalyst. Moreover, the fluorinated amide compound is applicable as a pressure-sensitive adhesive, binder, coating or other agent having excellent chemical resistance and solvent resistance.

EXAMPLE

Examples of the invention are given below by way of illustration and not by way of limitation. Me is methyl, and Ph is phenyl.

Example 1

A 300-ml separable flask equipped with a stirrer, thermometer, Dimroth condenser and dropping funnel was charged with 100.0 g of a compound of formula (13) shown below (vinyl convent=0.0122 mol/100 g), 100.0 g of 1,3-bistrifluoromethylbenzene, and 3.34 g of a compound of formula (14) shown below, which were homogeneously dissolved. To the flask, 0.10 g of a toluene solution of a catalyst in the form of chloroplatinic acid modified with $CH_2=CHSiMe_2OSiMe_2CH=CH_2$ (platinum concentration 0.5 wt %) was added dropwise. With stirring, reaction was conducted for one hour at 100° C. The reaction solution was stripped for about 2 hours under conditions: 160° C./5 mmHg, distilling off the reaction solvent. Subsequent cooling to room temperature yielded 103.3 g of a pale yellow clear gum-like compound. On analysis of the compound by $^1$H-NMR (TMS standard), Si—CH=CH$_2$ and Si—H groups were below the detection limit. The $^1$H—NMR (TMS standard) analysis confirmed the presence of Si—CH$_3$ (0.17 ppm), N—CH$_3$ (3.35 ppm), CF$_2$CH=CH$_2$ (5.7–6.1 ppm), and N—Ph—Si (7.0–7.6 ppm). An IR analysis (FIG. 1) revealed the absorption peak associated with C=O at 1690 cm$^{-1}$. From these analysis results, the compound was identified to be a polymer comprising recurring units of formula (15) shown below. A 10 wt % solution of the compound in nonafluorobutyl methyl ether (C$_4$F$_9$OCH$_3$) showed a kinematic viscosity of 18.3 mm$^2$/s.

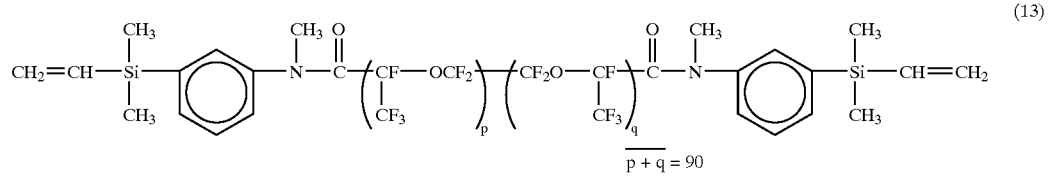

(13)

(14)

-continued

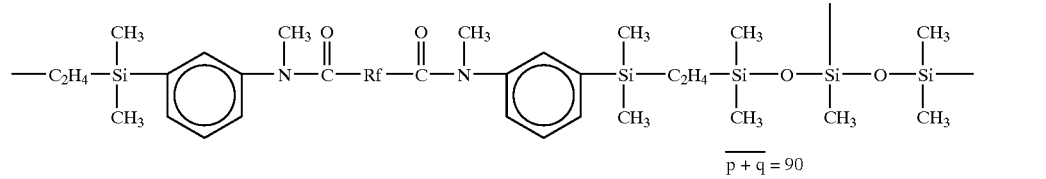

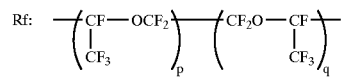

Example 2

Figure 2:
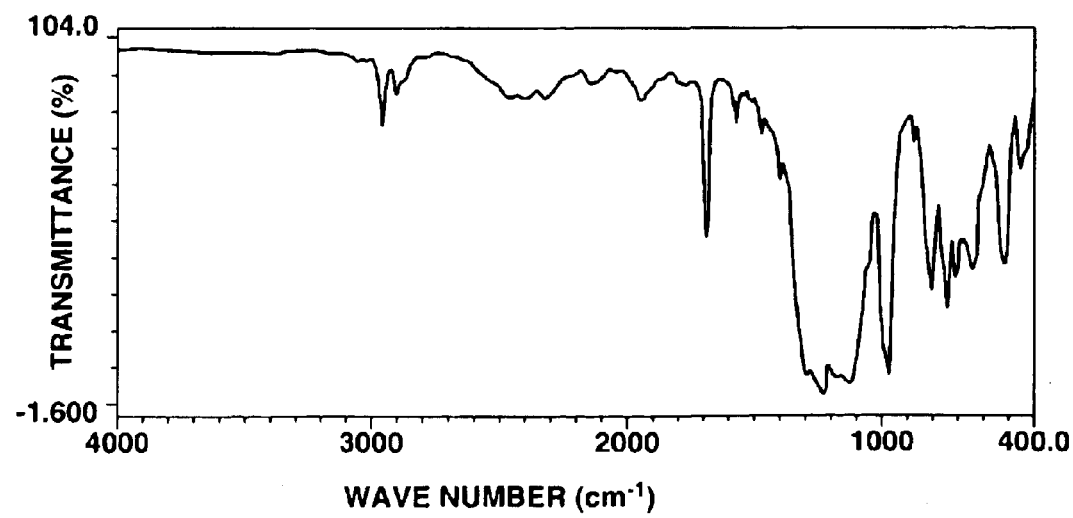

A 300-ml separable flask equipped with a stirrer, thermometer, Dimroth condenser and dropping funnel was charged with 100.0 g of a compound of formula (13) (vinyl convent=0.0122 mol/100 g), 100.0 g of 1,3-bistrifluoromethylbenzene, and 1.25 g of a compound of formula (16) shown below, which were homogeneously dissolved. To the flask, 0.10 g of a toluene solution of a catalyst in the form of chloroplatinic acid modified with $CH_2=CHSiMe_2OSiMe_2CH=CH_2$ (platinum concentration 0.5 wt %) was added dropwise. With stirring, reaction was conducted for one hour at 100° C. The reaction solution was stripped for about 2 hours under conditions: 160° C./5 mmHg, distilling off the reaction solvent. Subsequent cooling to room temperature yielded 101.2 g of a pale yellow clear gum-like compound. On analysis of the compound by $^1$H-NMR (TMS standard), Si—CH=CH$_2$ and Si—H groups were below the detection limit. The $^1$H—NMR (TMS standard) analysis confirmed the presence on Si—CH$_2$—Si (−0.19 ppm), Si—CH$_{13}$ (0.17 ppm), N—CH$_3$ (3.35 ppm), and N—Ph—Si (7.0–7.6 ppm). An IR analysis (FIG. 2) revealed the absorption peak associated with C=O at 1690 cm$^{-1}$. From these analysis results, the compound was identified to be a polymer comprising recurring units of formula (17) shown below. A 10 wt % solution of the compound in nonafluorobutyl methyl ether ($C_4F_9OCH_3$) showed a kinematic viscosity of 12.8 mm$^2$/s.

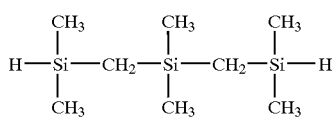

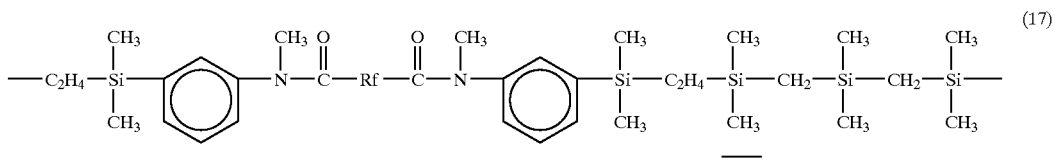

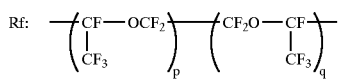

Example 3

Figure 3:
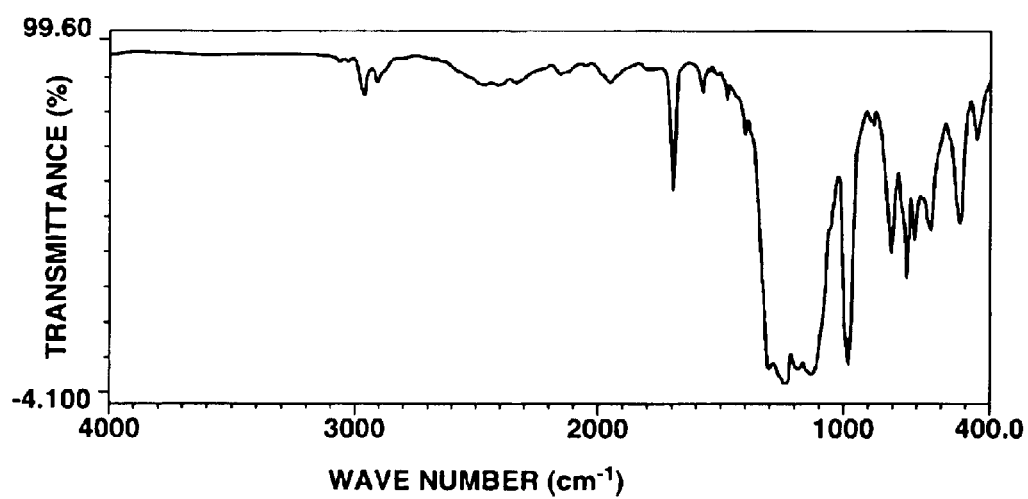

A 300-ml separable flask equipped with a stirrer, thermometer, Dimroth condenser and dropping funnel was charged with 100.0 g of a compound of formula (13) (vinyl convent=0.0122 mol/100 g), 100.0 g of 1,3-bistrifluoromethylbenzene, and 4.05 g of a compound of formula (18) shown below, which were homogeneously dissolved. To the flask, 0.10 g of a toluene solution of a catalyst in the form of chloroplatinic acid modified with $CH_2=CHSiMe_2OSiMe_2CH=CH_2$ (platinum concentration 0.5 wt %) was added dropwise. With stirring, reaction was conducted for one hour at 100° C. The reaction solution was stripped for about 2 hours under conditions: 160° C./5 mmHg, distilling off the reaction solvent. Subsequent cooling to room temperature yielded 104.0 g of a pale yellow clear gum-like compound. On analysis of the compound by $^1$H—NMR (TMS standard), Si—CH=CH$_2$ and Si—H groups were below the detection limit. The $^1$H—NMR (TMS standard) analysis confirmed the presence of Si—CH$_3$ (0.17 ppm), N—CH$_3$ (3.35 ppm), and N—Ph—Si (7.0–7.6 ppm). An IR analysis (FIG. 3) revealed the absorption with C=O at 1690 cm$^{-1}$.

From these analysis results, the compound was identified to be a polymer comprising recurring units of formula (19)

shown below. A 10 wt % solution of the compound in nonafluorobutyl methyl ether ($C_4F_9OCH_3$) showed a kinematic viscosity of 15.6 mm²/s.

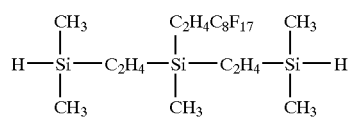
(18)

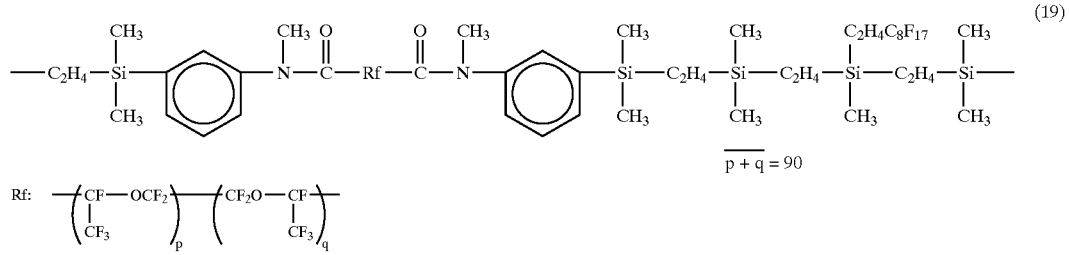
(19)

Rf:

There have been described fluorinated amide compounds having siloxane bonds or silalkylene bonds, which yield rubber having excellent chemical resistance and solvent resistance.

Japanese Patent Application No. 2001-245891 is incorporated herein by reference.

Although some preferred embodiments have been described, many modifications and variations may be made thereto in light of the above teachings. It is therefore to be understood that the invention may be practiced otherwise than as specifically described without departing from the

What is claimed is:

1. A fluorinated amide compound of the following general formula (1):

$$A—(Rf—Q)_n—Rf—A \qquad (1)$$

wherein Rf is a divalent perfluoroalkylene group $C_mF_{2m}$ wherein m is an integer of 2 to 15, or a divalent perfluorooxyalkylene group selected from groups of the following formulae (2), (3) and (4):

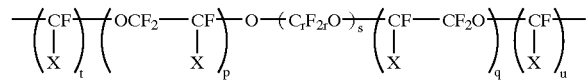
(2)

wherein X is each independently F or $CF_3$, p and q each are an integer of 0 to 200, r is an integer of 2 to 6, s is an integer of 1 to 6, t and u each are 1 or 2,

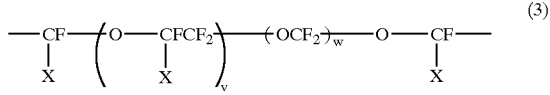
(3)

wherein X is as defined above, v and w each are an integer of 1 to 100,

(4)

wherein y is an integer of 1 to 200,
A is a monovalent organic group of the following formula (6):

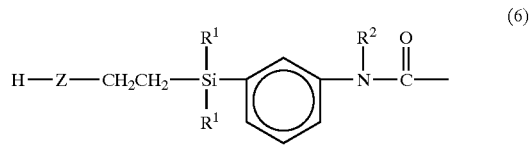
(6)

wherein $R^1$ is a monovalent hydrocarbon group selected from the group consisting of alkyl, cycloalkyl, aryl, aralkyl groups of 1 to 10 carbon atoms and substituted ones of the foregoing groups in which some or all of the hydrogen atoms are substituted with halogen atoms, $R^2$ is hydrogen or a monovalent hydrocarbon group selected from the group consisting of alkyl, cycloalkyl, aryl, aralkyl groups of 1 to 10 carbon atoms and substituted ones of the foregoing groups in which some or all of the hydrogen atoms are substituted with halogen atoms, Z is a divalent organic group of the following formula (7):

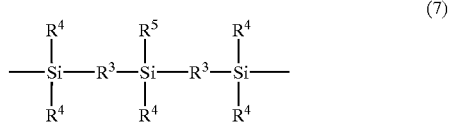
(7)

wherein $R^3$ is an oxygen atom or a divalent hydrocarbon group selected from the group consisting of alkylene, cycloalkylene, arylene groups of 1 to 8 carbon atoms, substituted ones of the foregoing groups in which some of the hydrogen atoms are substituted with halogen atoms, and combinations of alkylene with arylene, $R^4$ is a monovalent hydrocarbon group selected from the group consisting of alkyl, cycloalkyl, aryl, aralkyl groups of 1 to 10 carbon atoms and substituted ones of the foregoing groups in which some or all of the hydrogen atoms are substituted with halogen atoms, when $R^3$ is an oxygen atom, $R^5$ is an aliphatic unsaturation-bearing monovalent hydrocarbon group of 2 to 20 carbon atoms, when $R^3$ is a divalent hydrocarbon group, $R^5$ is a monovalent hydrocarbon group selected from the group consisting of alkyl, cycloalkyl, aryl, aralkyl groups of 1 to 10 carbon atoms, and substituted ones of the foregoing groups in which some or all of the hydrogen atoms are substituted with halogen atoms, Q is a divalent organic group of the following formula (8):

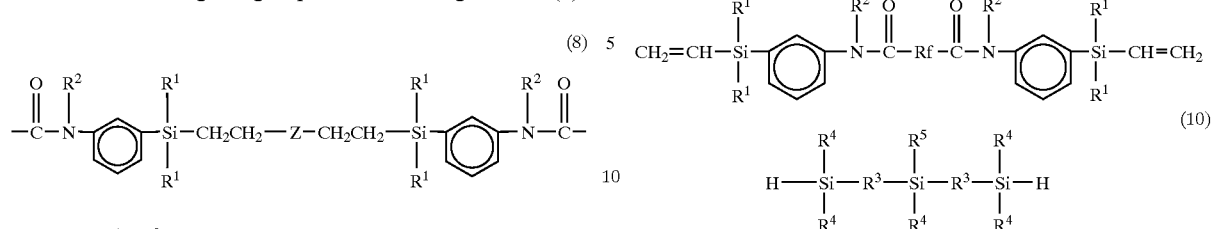

(8)

wherein $R^1$, $R^2$ and Z are as defined above, and n is an integer of at least 1.

2. A process of preparing a fluorinated amide compound of the general formula (1) as set forth in claim 1, comprising the step of effecting hydrosilylation reaction of a compound of the general formula (9) with a compound of the general formula (10):

wherein $R^1$ to $R^5$ and Rf are as defined in claim 1.

* * * * *